United States Patent
Nomura et al.

[11] Patent Number: 5,843,992
[45] Date of Patent: Dec. 1, 1998

[54] EPOXYSUCCINIC ACID DERIVATIVES

[75] Inventors: Yutaka Nomura, Chiba; Toshihiro Takahashi; Kaoru Hara, both of Saitama; Yasushi Yoshino; Mitsuo Masaki, both of Chiba, all of Japan

[73] Assignee: Nippon Chemiphar Co., Ltd., Tokyo, Japan

[21] Appl. No.: 930,509

[22] PCT Filed: Apr. 1, 1996

[86] PCT No.: PCT/JP96/00889

§ 371 Date: Sep. 29, 1997

§ 102(e) Date: Sep. 29, 1997

[87] PCT Pub. No.: WO96/30354

PCT Pub. Date: Oct. 3, 1996

[30] Foreign Application Priority Data

Mar. 31, 1995 [JP] Japan ................... 7-100504

[51] Int. Cl.⁶ ................ A61K 31/335; C07D 303/48
[52] U.S. Cl. ................ 514/475; 549/548; 549/549
[58] Field of Search ................ 549/548, 549; 514/475

[56] References Cited

U.S. PATENT DOCUMENTS 4,387,238  6/1983  Goi ............................ 549/549

*Primary Examiner*—Evelyn Huang
*Attorney, Agent, or Firm*—McAulay Nissen Goldberg Kiel & Hand, LLP

[57] ABSTRACT

An epoxysuccinic acid derivative having the following formula:

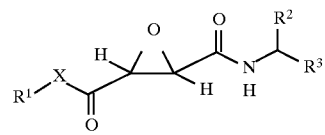

[wherein $R^1$ is hydrogen, alkyl, aryl, or aralkyl; each of $R^2$ and $R^3$ independently is aryl, aralkyl or alkyl; X is —O— or —$NR^4$—; and $R^4$ is hydrogen, alkyl, or aralkyl] is useful for prevention and treatment of bone diseases such as osteoporosis, malignant hypercalcemia and Paget's syndrome, and further useful for treatment of osteoarthritis and rheumatoid arthritis which are accompanied by abnormal enhancement of cathepsin L activity, and furthermore useful as a medicine for treating diseases in which cathepsin B and L participate, such as muscular dystrophy and muscular atrophy.

3 Claims, No Drawings

EPOXYSUCCINIC ACID DERIVATIVES

This application is the national phase of PCT/JP96/00889, filed Apr. 1, 1996, issued as WO 96/30354 on Oct. 3, 1996.

FIELD OF THE INVENTION

This invention relates to a novel epoxysuccinic acid derivative and a pharmaceutical composition for treating bone diseases using the same.

BACKGROUND OF THE INVENTION

In the bone tissue, bone resorption and bone formation are continuously and simultaneously performed by osteoclasts and osteoblasts, respectively. The structure and amount of the bone is kept on their balance. However, excessive bone resorption causes bone diseases such as osteoporosis, malignant hypercalcemia, and Pajet's syndrome.

The process of bone resorption (i.e., decalcification) by osteoclasts can be divided into two steps, namely, dissolution of minerals and degradation of bone substrate. The degradation of bone substrate is considered to occur by the action of lysosomal enzymes. According to recent studies, it is recognized that among the lysosomal enzymes, cathepsin L and its analogous enzymes, which are cysteine proteases, play a key role [Kakegawa and Katsunuma, Molecular Medicine, 30(10), 1310–1318 (1993), and Tezuka et al., J. Biol. Chem., 269, 1106–1109(1994)]. Further, it has been reported that a cysteine protease inhibitor blocks the bone resorption [J. M. Delaisse et al., Biochem. Biophys., Res. Commun., 125, 441–447(1984)]. Therefore, compounds which inhibit action of cysteine protease such as cathepsin L are considered to be of value for treating bone diseases such as osteoporosis.

For instance, it has been already proposed that certain epoxysuccinic acid derivatives be employed for treating bone diseases [Japanese Patent Provisional Publications No. 63-284127 and No. H2-218610]. However, there have been no reports on the clinical study of the cysteine protease inhibitors, and the study has been recently started.

Japanese Patent Publication No. 61-55509 discloses epoxysuccinic acid derivatives (epoxysuccinum acid compounds) as protease inhibitors in which a thiol group participates in their action. There are given no disclosures, however, with respect to compounds which has a branched chain on the carbon atom adjacently connected to the nitrogen atom of N-substituted carbamoyl group which is attached to the oxirane ring, for instance, diphenylmethylcarbamoyl and (3-methyl-1-phenylbutyl)carbamoyl.

SUMMARY OF THE INVENTION

It is an object of the present invention to provide a compound and a pharmaceutical composition which are useful for prevention and treatment of bone diseases such as osteoporosis, malignant hypercalcemia and Paget's syndrome.

It is another object of the invention to provide a compound and a pharmaceutical composition which are useful for treating osteoarthritis and rheumatoid arthritis which are accompanied by abnormal enhancement of cathepsin L activity.

It is a further object of the invention to provide a compound which is useful as a medicine for treating diseases in which cathepsin B and L participate, such as muscular dystrophy and muscular atrophy.

The present inventors have earnestly studied to solve the above-mentioned problems and have found that the epoxysuccinic acid derivative or its salt which is represented by the below-mentioned formula (I) and has a characteristic feature in that the substituent of the amide group on the right side are branched has an activity of inhibiting bone resorption superior to the epoxysuccinic acid derivatives described in the aforementioned Japanese Patent Publication No. 61-55509, and that it is useful for prevention and treatment of bone diseases. The present invention has been accomplished based on the above finding. The typical activity of the compound of Japanese Patent Publication No. 61-55509 is shown by the comparative compounds X and Y in the hereinafter given in the comparative experiments.

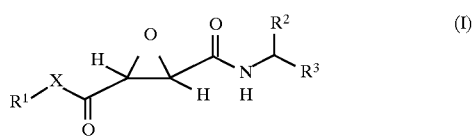

in which $R^1$ represents a hydrogen atom, an alkyl group having 1 to 30 carbon atoms, an aryl group having 6 to 40 carbon atoms, or an aralkyl group having 7 to 40 carbon atoms; each of $R^2$ and $R^3$ independently represents an aryl group having 6 to 40 carbon atoms, an aralkyl group having 7 to 20 carbon atoms, or an alkyl group having 3 to 10 carbon atoms; X represents —O— or —NR$^4$—; and $R^4$ represents a hydrogen atom, an alkyl group having 1 to 10 carbon atoms, or an aralkyl group having 7 to 20 carbon atoms.

PREFERRED EMBODIMENTS OF THE INVENTION

The epoxysuccinic acid derivative of the following formula (I) is further described.

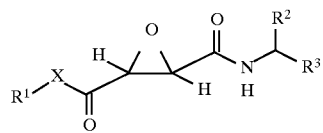

In the above formula, $R^1$ is a hydrogen atom, an alkyl group, an aryl group or an aralkyl group. Preferred are a hydrogen atom, an alkyl group and an aralkyl group. The alkyl group, aryl group and aralkyl group may have a substituent (e.g., hydroxyl group, a halogen atom, an alkyl group having 1 to 10 carbon atoms, an alkoxy group having 1 to 10 carbon atoms, and an aryl group having 6 to 20 carbon atoms).

The alkyl group preferably contains 1 to 30 carbon atoms (total carbon atom number including carbon atom number of substituent, if the substituent is attached), more preferably 1 to 15 carbon atoms, most preferably 1 to 6 carbon atoms. The alkyl group may have a chain structure or a cyclic structure. The alkyl group having a chain structure may be in the branched form.

The aryl group preferably contains 6 to 40 carbon atoms (total carbon atom number including carbon atom number of substituent, if the substituent is attached), more preferably 6 to 30 carbon atoms, most preferably 6 to 20 carbon atoms. Examples of the aryl groups include phenyl and naphthyl.

The aralkyl group preferably contains 7 to 40 carbon atoms (total carbon atom number including carbon atom number of substituent, if the substituent is attached), more preferably 7 to 30 carbon atoms, most preferably 7 to 20 carbon atoms. Examples of the aralkyl groups include benzyl, phenethyl and diphenylmethyl.

Each of $R^2$ and $R^3$ of the above-mentioned formula independently is an aryl group, an aralkyl group, or an alkyl group having 3 to 10 carbon atoms. Each of the alkyl group, aryl group and aralkyl group may have a substituent (e.g., a hydroxyl group, a halogen atom, an alkyl group having 1 to 10 carbon atoms, an alkoxy group having 1 to 10 carbon atoms, and an aryl group having 6 to 20 carbon atoms).

The aryl group preferably contains 6 to 40 carbon atoms (total carbon atom number including carbon atom number of substituent, if the substituent is attached), more preferably 6 to 30 carbon atoms, most preferably 6 to 20 carbon atoms. Examples of the aryl groups include phenyl and naphthyl.

The alkyl group contains 3 to 10 carbon atoms (total carbon atom number including carbon atom number of substituent, if the substituent is attached). The alkyl group more preferably contains 3 to 6 carbon atoms. The alkyl group may have a chain structure or a cyclic structure. The alkyl group having a chain structure may be in the branched form.

The aralkyl group preferably contains 7 to 20 carbon atoms (total carbon atom number including carbon atom number of substituent, if the substituent is attached), more preferably 7 to 15 carbon atoms, most preferably 7 to 10 carbon atoms. Examples of the aralkyl groups include benzyl and phenethyl.

In the aforementioned formula, X is —O— or —$NR^4$—. $R^4$ is a hydrogen atom, an alkyl group, or an aralkyl group, and preferably is a hydrogen atom or an alkyl group. Most preferred is a hydrogen atom. The alkyl group and aralkyl group may have the same substituent as mentioned above.

The alkyl group for $R^4$ preferably contains 1 to 10 carbon atoms (total carbon atom number including carbon atom number of substituent, if the substituent is attached), more preferably 1 to 6 carbon atoms, most preferably 1 to 4 carbon atoms. The alkyl group preferably has a chain structure. The alkyl group having a chain structure may be in the branched form.

The aralkyl group for $R^4$ preferably contains 7 to 20 carbon atoms (total carbon atom number including carbon atom number of substituent, if the substituent is attached), more preferably 7 to 15 carbon atoms, most preferably 7 to 10 carbon atoms. Examples of the aralkyl groups include benzyl and phenethyl.

The two carbon atoms of the oxirane ring of the aforementioned formula both are asymmetric carbon atoms. The aforementioned formula means that the two carbonyl groups attached to the oxirane ring are in the trans conformation. Therefore, the epoxysuccinic acid derivative of the invention can be either an optical isomer in the form of the below-mentioned (T1) or in the form of the below-mentioned (T2), or a mixture thereof.

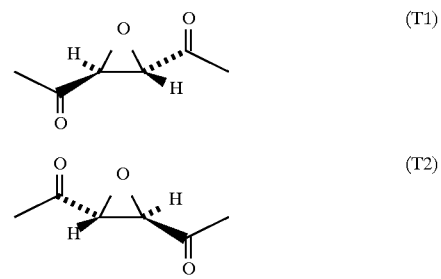

Examples of the epoxysuccinic acid derivatives of the invention are set forth in the following Table 1, wherein $R^1$, $R^2$, R3 and X mean those shown in the aforementioned formula.

TABLE 1

| Compound | $R^1$ | X | $R^2$ | $R^3$ |
|---|---|---|---|---|
| 1 | H | —O— | phenyl | phenyl |
| 2 | ethyl | —O— | phenyl | phenyl |
| 3 | isobutyl | —O— | phenyl | phenyl |
| 4 | cyclohexyl | —O— | phenyl | phenyl |
| 5 | benzyl | —O— | phenyl | phenyl |
| 6 | diphenylmethyl | —O— | phenyl | phenyl |
| 7 | H | —O— | p-chlorophenyl | p-chlorophenyl |
| 8 | ethyl | —O— | p-methoxyphenyl | p-methoxyphenyl |
| 9 | H | —O— | isopentyl | isopentyl |
| 10 | ethyl | —O— | isopentyl | isopentyl |
| 11 | cyclohexyl | —O— | isopentyl | isopentyl |
| 12 | ethyl | —NH— | phenyl | phenyl |
| 13 | ethyl | —NH— | isopentyl | isopentyl |
| 14 | ethyl | —NEt— | phenyl | phenyl |
| 15 | diphenylmethyl | —NH— | phenyl | phenyl |
| 16 | (branched alkyl structure) | —NH— | isopentyl | isopentyl |
| 17 | H | —O— | isopropyl | isopropyl |
| 18 | H | —O— | benzyl | benzyl |
| 19 | H | —O— | phenyl | isobutyl |
| 20 | H | —O— | phenyl | isopropyl |
| 21 | ethyl | —O— | phenyl | isobutyl |

TABLE 1-continued

| Compound | R¹ | X | R² | R³ |
|---|---|---|---|---|
| 22 | H | —NH— | benzyl | benzyl |
| 23 | H | —O— | phenyl | benzyl |

The epoxysuccinic acid derivative of the invention can be employed in the form of a salt. In the case that $R^1$ is a hydrogen atom and X is —O—, a carboxyl group can be formed in combination with the carbonyl attached to the oxirane ring and can form a salt with a base. Examples of cations of the base include ions of alkali metals (e.g. sodium, and potassium) and ions of alkaline earth metals (e.g., calcium).

The epoxysuccinic acid derivative of the invention can be easily synthesized by processes analogous to the synthesis processes described in Japanese Patent Publication No. 61-55509 and Japanese Patent Provisional Publication No. 52-31024, or by the processes as described in the hereinafter mentioned Examples 1 to 10 or in a manner similar to these processes.

The pharmacological effects of the epoxysuccinic acid derivative of the invention are described below.

The epoxysuccinic acid derivative of the invention is a compound having inhibitory activities against thiol protease. The thiol proteases encompass cathepsin L and cathepsin B, or calpain. Therefore, the epoxysuccinic acid derivative of the invention and its physiologically acceptable salt are expected to show pharmacological effects on diseases in which the proteases participate.

As described in the explanation of prior art, examples of diseases in which cathepsin L participates include bone diseases such as osteoporosis, malignant hypercalcemia, and Paget's syndrome. Therefore, the epoxysuccinic acid derivative of the invention and its physiologically acceptable salt are useful as medicines for preventing or treating these bone diseases.

It is reported that cathepsin L degradate collagen Type II, Type IX, and Type XI constituting articular cartilage in the neutral region [FEBS Lett., 269, 189–193(1990)]. Therefore, the epoxysuccinic acid derivative of the invention and its physiologically acceptable salt are expected to be useful in treating osteoarthritis and rheumatoid arthritis which are accompanied by abnormal enhancement of cathepsin L activity (see Japanese Patent Provisional Publication H5-178757).

The epoxysuccinic acid derivative of the invention is also effective as a cathepsin B inhibitor.

In more detail, examples of diseases in which thiol proteases other than cathepsin L, such as cathepsin B, participates include muscular dystrophy and muscular atrophy (in which cathepsin B and calpain participate), Alzheimer's disease (in which calpain participates), and diseases which are considered to be caused by demyelination of neurocyte, such as multiple sclerosis and neuropathy of peripheral nervous system (in which calpain participates), cataract (in which calpain participates), allergic disorder (in which thiol protease participates), fulminant hepatitis (in which calpain participates), breast cancer, prostatic cancer, and prostatomegaly (in which calpain participates), hyperplasia and metastasis of cancer (in which cathepsin B and calpain participate), aggregation of platelet (in which calpain participates) (see Japanese Patent Provisional Publication H6-239835). Therefore, the epoxysuccinic acid derivative of the invention is considered to be useful for treating and preventing these diseases.

The epoxysuccinic acid derivative of the invention and its physiologically acceptable salt are expected to be useful for prevention and treatment of the above-mentioned diseases. Particularly, it is useful for prevention and treatment of bone diseases such as osteoporosis, malignant hypercalcemia, and Paget's syndrome.

The epoxysuccinic acid derivative of the invention can be administered through either oral or parenteral route. The orally administrable composition can be prepared in the form of tablets, capsules, powder, granules, or syrup. The parenteral administration can be performed through mucosal membrane, body surface, blood vessel, or tissue. The mucosal administration can be performed using ophthalmic solutions, inhalant, spray, or suppository. The surface administration can be performed using ointment. The administration through blood vessel and tissue can be performed using injections.

The orally administrable composition can be prepared using conventional excipient, disintegrator, binder, lubricant, dye and diluent. The excipient generally is glucose or lactose. The disintegrator can be starch or carboxymethyl cellulose calcium. The lubricant can be magnesium stearate or talc. The binder can be hydroxy-propyl cellulose, gelatin, or polyvinyl alcohol.

The pharmaceutical composition for parenteral administration can be prepared in the conventional way. For instance, the injection can be prepared using an ordinary distilled water for injection, physiological saline, or Ringer's solution.

The dosage of the epoxysuccinic acid derivative of the invention is in the range of 0.01 mg to 100 m/day for adult in the case of using injections. In the case of oral administration, the dosage is in the range of 0.1 to 1 g/day for adult. The dosage can be increased or decreased depending on age, race, and conditions of patients.

EXAMPLE 1

Ethyl (2S,3S)-3-diphenylmethylcarbamoyloxirane-2-carboxylate (Compound No. 2)

To a solution of (2S,3S)-3-ethoxycarbonyloxirane-2-carboxylic acid (8.01 g, 50.0 mmol.) in ethyl acetate (120 mL) was added N-hydroxysuccinimide (5.76 g, 50.0 mmol.) and then added N,N'-dicyclohexylcarbodiimide (5.75 g, 50.0 mmol) under chilling with ice. The resulting mixture was stirred at 5° C. for one hour, and to the mixture was a solution of aminodiphenylmethane (9.17 g, 50.0 mmol.) in ethyl acetate (30 mL). The mixture was stirred at 5° C. for one hour and then at room temperature for one hour. The resulting N,N'-dicyclohexylurea (DC-Urea) was removed by filtration, and the filtrate was washed successively with 1N hydrochloric acid, an aqueous sodium hydrogen carbonate saturated solution, and an aqueous sodium chloride saturated solution, and then dried over anhydrous sodium sulfate. The solvent was distilled off under reduced pressure, and the residue was recrystalized from ethyl acetate—n-hexane, to give the desired compound as a white crystalline product (1.25 g, yield: 77%).

¹H-NMR (400 MHz, CDCl₃)δ: 1.32 (3H, t, J=7 Hz), 3.51 (1H, d, J=2 Hz), 3.77 (1H, d, J=2 Hz), 4.2–4.3 (2H, m), 6.22 (1H, d, J=8 Hz), 6.67 (1H, d, J=8 Hz), 7.1–7.4 (10H, m).

EXAMPLE 2

(2S,3S)-3-Diphenylmethylcarbamoyloxirane-2-carboxylic acid (Compound No. 1)

In ethanol (300 mL) was dissolved ethyl (2S,3S)-3-diphenylmethylcarbamoyloxirane-2-carboxylate (5.50 g, 16.9 mmol.) obtained in Example 1. To the resulting solution was added a solution of 0.5N sodium hydroxide in ethanol (40.4 mL, 20.2 mmol.), and the mixture was stirred for 3 hours at room temperature. The solvent was distilled off under reduced pressure, and washed with two 100 mL portions of ethyl ether after addition of water (300 mL). The aqueous portion was made to show pH 1–2 by addition of 2N hydrochloric acid, and extracted with three 100 mL portions of ethyl acetate. The organic portion was washed with an aqueous sodium chloride saturated solution and dried over anhydrous sodium sulfate. The solvent was distilled off under reduced pressure to give the desired compound as a white crystalline powdery product (4.76 g, yield: 95%).

¹H-NMR (400 MHz, CD₃OD)δ: 3.57 (1H, d, J=2 Hz), 3.71 (1H, d, J=2 Hz), 6.23 (1H, s), 7.2–7.4 (10H, m).

EXAMPLE 3

Sodium (2S,3S)-3-diphenylmethylcarbamoyloxirane-2-carboxylate (Sodium salt of Compound No. 1)

In ethyl acetate (10 mL) was dissolved the compound (100 mg, 0.336 mmol.) obtained in Example 2. To the resulting solution was added a solution of sodium hydrogen carbonate (28.2 mg, 0.336 mmol.) in water (10 mL). The mixture was vigorously shaken. The aqueous portion was taken, and concentrated to dryness under reduced pressure to give the desired compound as a white powdery product (106 mg., yield: 99%).

¹H-NMR (400 MHz, D₂O)δ: 3.47 (1H, d, J=2 Hz), 3.63 (1H, d, J=2 Hz), 6.15 (1H, s), 7.3–7.5 (10H, m).

IR (KBr) cm⁻¹: 3412, 3219, 3064, 3030, 1670, 1632, 1552, 1495, 1454, 1448, 1398, 1317, 1285, 1248, 1093, 1086, 1051, 1030, 1007, 960, 899, 862, 783, 758, 742, 698, 677, 642, 602, 571, 482.

EXAMPLE 4

(2S,3S)-N-Ethyl-3-diphenylmethylcarbamoyloxirane-2-carboxamide (Compound No. 12)

To a solution of (2S,3S)-3-diphenylmethylcarbamoyloxirane-2-carboxylic acid (1.80 g, 6.05 mmol.) and N-hydroxysuccinimide (696 mg, 6.05 mmol) in methylene chloride (10 mL) was added a solution of N,N'-dicyclohexylcarbodiimide (1.25 g, 6.05 mmol.) in methylene chloride (7 mL) under chilling with ice. The mixture was stirred for 30 minutes at room temperature. To the mixture was then added under chilling with ice a solution of ethylamine hydrochloride (493 mg, 6.05 mmol.) and triethylamine (0.84 mL, 6.05 mmol) in methylene chloride (7 mL). The resulting mixture was stirred overnight at 5° C. The solvent was distilled off under reduced pressure, and N,N'-dicyclohexylurea (DC-Urea) was removed by filtration after addition of ethyl acetate (10 mL). The solution was washed successively with water, 0.5N hydrochloric acid, an aqueous sodium hydrogen carbonate saturated solution, and an aqueous sodium chloride saturated solution, and dried over anhydrous sodium sulfate. The solvent was distilled off under reduced pressure, and the residue was purified by medium pressure silica gel column chromatography (chloroform/methanol=1/0 to 50/1), to give the desired compound as a white crystalline powdery product (928 mg, yield: 47%).

m.p.: 190.0°–195.0° C. (decomp.)

¹H-NMR (400 MHz, CDCl₃)δ: 1.14 (3H, t), 3.30 (2H, dq), 3.51 (1H, d), 3.55 (1H, d), 5.95 (1H, br.s), 6.22 (1H, d, J=8 Hz), 6.59 (1H, br.d, J=8 Hz), 7.1–7.4 (10H, m).

IR (KBr) cm⁻¹: 3290, 3088, 3064, 3030, 2980, 2933, 2773, 1653, 1551, 1495, 1452, 1446, 1371, 1354, 1279, 1240, 1153, 1092, 1053, 1030, 999, 960, 891, 864, 862, 847, 808, 754, 696, 648, 598, 571, 536, 478.

EXAMPLE 5

Ethyl (2S,3S)-3-[[4-methyl-1-(3-methylbutyl)pentyl]-carbamoyl]oxirane-2-carboxylate (Compound No. 10)

In benzene (40 mL) was suspended potassium (2S,3S)-3-ethoxycarbonyloxirane-2-carboxylate (1.98 g, 10.0 mmol.). The benzene (13 mL) was distilled off under atmospheric pressure to remove water. The residual solution was cooled to room temperature. The solution was stirred, and to the stirred solution was dropwise added thionyl chloride (0.88 mL, 12.0 mmol). The mixture was heated under reflux for 2.5 hours to give a solution of an acid chloride of the starting compound.

In a dry benzene (10 mL) were dissolved 4-methyl-1-(3-methylbutyl)pentylamine (2.06 g, 12.0 mmol.) and triethylamine (1.67 mL, 12.0 mmol.). To the resulting solution was dropwise added the above-mentioned acid chloride solution under chilling with ice. The mixture was then stirred for 3 hours at room temperature. To the mixture was added water (3 mL), and the organic portion was taken. The organic portion was washed successively with an aqueous 10% citric acid solution, water, an aqueous sodium hydrogen carbonate saturated solution, water, and an aqueous sodium chloride saturated solution, and dried over anhydrous sodium sulfate. The solvent was distilled off under reduced pressure, and the residue was purified by medium pressure silica gel column chromatography (hexane/ethyl acetate=5/1) to give the desired compound as a yellow oil (1.40 g, yield: 45%).

¹H-NMR (400 MHz, CDCl₃)δ: 0.8–1.0 (12H, m), 1.1–1.4 (6H, m), 1.32 (3H, t, J=7 Hz), 1.4–1.6 (4H, m), 3.42 (1H, d, J=2 Hz), 3.68 (1H, d, J=2 Hz), 3.83 (1H, m), 4.2–4.3 (2H, m), 5.78 (1H, d, J=9 Hz).

EXAMPLE 6

(2S,3S)-3-[[4-Methyl-1-(3-methylbutyl)pentyl]carbamoyl]oxirane-2-carboxylic acid (Compound No. 9)

The reactions and treatments of Example 2 were repeated using the compound (1.40 g, 4.47 mmol.) obtained in Example 5 and a solution of 0.5N potassium hydroxide in ethanol (10.7 mL, 5.35 mmol.), to give the desired compound as a pale yellow amorphous product (1.15 g, yield: 90%).

¹H-NMR (400 MHz, CDCl₃)δ: 0.8–0.9 (12H, m), 1.0–1.4 (6H, m), 1.4–1.6 (4H, m), 3.46 (1H, d, J=2 Hz), 3.78 (1H, d, J=2 Hz), 3.84 (1H, m), 6.12 (1H, d, J=9 Hz).

EXAMPLE 7

Sodium (2S,3S)-3-[[4-methyl-1-(3-methylbutyl)pentyl]-carbamoyl]oxirane-2-carboxylate (Sodium salt of Compound No. 9)

The reactions and treatments of Example 3 were repeated using the compound (111 mg, 0.389 mmol.) obtained in Example 6 and sodium hydrogen carbonate (32.7 mg, 0.389 mmol.), to give the desired compound as a pale yellow powdery product (yield: 75%).

$^1$H-NMR (400 MHz, D$_2$O)δ: 0.8–1.0 (12H, m), 1.1–1.3 (4H, m), 1.4–1.7 (6H, m), 3.42 (1H, s), 3.51 (1H, s), 3.75 (1H, m).

IR (KBr) cm$^{-1}$: 3417, 3253, 3093, 2954, 2870, 1660, 1560, 1468, 1435, 1398, 1367, 1317, 1255, 1223, 1171, 962, 895, 852, 795, 744, 712, 679, 482.

EXAMPLE 8

Ethyl (2R,3R)-3-[(3-methyl-1-phenylbutyl)carbamoyl]-oxirane-2-carboxylate (Compound No. 21)

The reactions and treatments of Example 5 were repeated using potassium (2R,3R)-3-ethoxycarbonyloxirane-2-carboxylate (3.97 g, 20.0 mmol.), thionyl chloride (2.86 g, 24.0 mmol), 3-methyl-1-phenylbutylamine (4.25 g, 26.0 mmol), and triethylamine (2.63 g, 26.0 mmol.), to give the desired compound as a colorless viscous oil (5.86 g, yield: 96%).

$^1$H-NMR (400 MHz, CDCl$_3$)δ: 0.92 (1.5H, d, J=7 Hz), 0.93 (1.5H, d, J=7 Hz), 0.94 (1.5H, d, J=7 Hz), 0.95 (1.5H, d, J=7 Hz), 1.25 (1.5H, t, J=7 Hz), 1.31 (1.5H, t, J=7 Hz), 1.4–1.7 (3H, m), 3.33 (0.5H, d, J=2 Hz), 3.47 (0.5H, d, J=2 Hz), 3.65 (0.5H, d, J=2 Hz), 3.68 (0.5H, d, J=2 Hz), 4.2–4.3 (2H, m), 5.02 (1H, m), 6.21 (1H, br. d, J=8 Hz), 7.2–7.4 (5H, m).

EXAMPLE 9

(2R,3R)-3-[(3-Methyl-1-phenylbutyl)carbamoyl]oxirane-2-carboxylic acid (Compound No. 19)

The reactions and treatments of Example 2 were repeated using the compound (2.13 g, 6.98 mmol.) obtained in Example 8 and a solution of 0.5N potassium hydroxide in ethanol (18 mL, 9.0 mmol.), to give the desired compound as a white amorphous product (1.78 g, yield: 92%).

$^1$H-NMR (400 MHz, CDCl$_3$)δ: 0.8–1.0 (6H, m), 1.4–1.8 (3H, m), 3.34 (0.5H, d, J=2 Hz), 3.47 (0.5H, d, J=7 Hz), 3.67 (0.5H, d, J=2 Hz), 3.71 (0.5H, d, J=2 Hz), 5.00 (1H, dt, J=8,8 Hz), 6.63 (0.5H, d, J=8,8 Hz), 6.66 (0.5H, d, J=8 Hz), 7.1–7.4 (5H, m), 8.19 (1H, brs).

EXAMPLE 10

Sodium (2R,3R)-3-[(3-methyl-1-phenylbutyl)carbamoyl]-oxirane-2-carboxylate (Sodium salt of Compound No. 19)

The reactions and treatments of Example 3 were repeated using the compound (1.70 g, 6.18 mmol.) obtained in Example 9 and sodium hydrogen carbonate (515 mg, 6.13 mmol.), to give the desired compound as a pale yellow powdery product (1.76 g, yield: 96%).

$^1$H-NMR (400 MHz, D$_2$O)δ: 0.9–1.0 (6H, m), 1.5–1.8 (3H, m), 3.41 (1H, m), 3.55 (1H, m), 4.93 (1H, m), 7.3–7.5 (5H, m).

EXAMPLE 11

Ethyl (2S,3S)-3-[(α-benzylphenethyl)carbamoyl]oxirane-2-carboxylate

The reactions and treatments of Example 1 were repeated using (2S,3S)-3-ethoxycarbonyloxirane-2-carboxylic acid (1.01 g, 6.31 mmol.), N-hydroxysuccimide (726 mg, 6.31 mmol.), N,N'-dicyclohexylcarbodiimide (1.30 g, 6.31 mmol.), and α-benzylphenethylamine (1.43 g, 6.31 mmol.). Thus prepared product was purified by silica gel column chromatography (chloroform/methanol=50/1) to give the desired compound as a pale yellow oil (2.22 g, yield: quantitatively).

$^1$H-NMR (400 MHz, CDCl$_3$)δ:
1.30 (3H, t, J=7 Hz), 2.65 (1H, dd, J=9, 14 Hz), 2.86 (2H, d, J=7 Hz), 2.87 (1H, d, J=2 Hz), 2.92 (1H, dd, J=6, 14 Hz), 3.51 (1H, d, J=2 Hz), 4.2–4.3 (2H, m), 4.42 (1H, m), 5.78 (1H, br. d, J=9 Hz), 7.1–7.3 (10H, m).

EXAMPLE 12

(2S,3S)-3-[(α-Benzylphenethyl)carbamoyl]oxirane-2-carboxylic acid

The reactions and treatments of Example 2 were repeated using the compound (2.22 g, 6.28 mmol.) obtained in Example 11 and a solution of 5N potassium hydroxide in ethanol (15.1 mL, 7.55 mmol), to give the desired compound as a white amorphous product (1.78 g, yield: 87%).

$^1$H-NMR (400 MHz, D$_2$O)δ: 2.6–2.8 (2H, m), 2.89 (1H, s), 3.0–3.1 (2H, m), 3.22 (1H, s), 4.33 (1H, m), 7.2–7.4 (10H, m).

EXAMPLE 13

Sodium (2S,3S)-3-[(α-benzylphenethyl)carbamoyl]oxirane-2-carboxylate

The reactions and treatments of Example 3 were repeated using the compound (1.78 g, 5.47 mmol.) obtained in Example 12 and sodium hydrogen carbonate (460 mg, 5.47 mmol.), to give the desired compound as a white powdery product (1.77 g, yield: 93%).

$^1$H-NMR (400 MHz, D$_2$O)δ: 2.7–2.8 (2H, m), 2.90 (1H, d, J=2 Hz), 3.0–3.1 (2H, m), 3.23 (1H, d, J=2 Hz), 4.34 (1H, m), 7.2–7.4 (10H, m).

IR (KBr) cm$^{-1}$: 3398, 3246, 3089, 3026, 2956, 2927, 2860, 1668, 1626, 1566, 1497, 1454, 1396, 1311, 1259, 1215, 1119, 1084, 1028, 982, 957, 897, 864, 847, 798, 746, 698, 677, 607, 519, 492.

EXAMPLE 14

Bone Resorption Inhibitory Activity

From ICR mouse (age: 6 to 7 days), calvaria was taken under aseptic conditions. The calvaria was divided along the median line into two parts after its connective tissue was removed. In a culture medium (modified BGjb medium, containing 5% inactivated bovine fetal serum) in an amount of 1 mL per a pair of bones, a pre-culture was performed for 24 hours under the conditions of 5% CO$_2$ and 37° C. After the pre-culture was complete, each one of bone was placed in 0.5 mL of the same culture medium containing the test compound of different concentration, and cultured for 72 hours in the presence of 3×10$^{-7}$M parathyroid hormone (PTH). For the control, culture was performed in the same manner except for using neither test compound nor PTH.

After the culture was complete, the amount of calcium released in the supernatant of the culture medium in the 72 hour culture as well as the amount of calcium contained in the bone (dissolved in 1 mL of 6N hydrochloric acid) were determined by ortho-cresol phthalein complexon (OCPC) method.

The calcium release ratio (%) was calculated according to the following equation:

$$\text{Release ratio (\%)} = \frac{\text{[Ca amount released in the culture medium]}}{\text{[Ca amount released in the culture medium + Ca amount in the bone]}} \times 100$$

The inhibition ratio (%) of bone resorption by the test compound was calculated according to the following equation:

$$\text{Inhibition ratio (\%)} = [1 - \frac{\text{(Release ratio in the presence of PTH and test compound} - \text{Release ratio of Control)}}{\text{(Release ratio in the presence of PTH} - \text{Release ratio of Control)}}] \times 100$$

The results are set forth in Table 2.

EXAMPLE 15

Cathepsin L Inhibitory Action (1) Preparation of Rat Liver Lysosome Fraction

Male rat of Wistar strain was killed by exsangulnation and a ice-chilled physiological saline was introduced into portal vein for circulation. Then, its liver was taken out. Thereafter, the following procedures were performed at 4° C.

The liver was minced by scissors. Five grams of minced liver were homogenized in a Potter type Teflon Homogenizer after addition of 0.25M aqueous sucrose solution in a volume as much as nine times. The homogenized mixture was centrifuged for 10 minutes at 800 G. The resulting supernatant was further centrifuged at 12,000 G for 20 minutes. The precipitate was homogenized in 25 mL of 0.25M aqueous sucrose solution, and then centrifuged for 20 minutes at 12,000 G. The resulting precipitate was further homogenized after 100 mL of 0.25M aqueous sucrose solution. Thus, a lysosome fraction was obtained.

The lysosome fraction was diluted with 0.25M aqueous sucrose solution containing 0.33% of Triton X-100 for the use in the measurement of cathepsin L activity.

(2) Measurement of Cathepsin L Activity

To 0.25 mL of a solution (pH: 5.5) containing 340 mM sodium acetate, 60 mM acetic acid, 4 mM EDTA and 8 mM dithiothreitol were added 0.1 mL of the lysosome fraction, 5 μL of the test compound solution, and 0.545 mL of distilled water. The mixture was preincubated at 30° C. for 15 minutes. Thereafter, 0.1 mL of 50 μM carbobenzoxy-L-phenylalanyl-L-arginine-4-methylcoumaryl-7-amide (Z-Phe-Arg-MCA) solution was added, and the reaction was started. The reaction was performed at 30° C. for 20 minutes, and then terminated by addition of 1 mL of an aqueous solution (pH: 4.3) containing 100 mM sodium monochloroacetate, 30 mM sodium acetate and 70 mM acetic acid. The finally obtained solution was subjected to measurement of fluorescence strength (excitation wavelength: 380 nm, emission wavelength: 460 nm).

The Z-Phe-Arg-MCA is also decomposed by cathepsin B which is contained in the lysosome fraction. Therefore, the measurement was performed in the presence of $10^{-7}$M CA-074 [Murata, et al., FEBS Lett., 280, 307–310 (1991)] which was known as a cathepsin B specific inhibitor, so that the cathepsin B activity was completely inhibited.

The results of Examples 14 and 15 are given in the following Table 2.

TABLE 2

| Test Compound | Bone Resorption Inhibition (Concentration of Test Comp.) | | | Cathepsin L Inhibition |
|---|---|---|---|---|
| | $10^{-6}$M | $10^{-5}$M | $10^{-4}$M | $IC_{50}$ (M) |
| Example 3 | 90 | 82 | 95 | $2.4 \times 10^{-7}$ |
| Example 7 | 63 | 87 | 82 | $1.9 \times 10^{-8}$ |
| Comparison X | 25 | 40 | 66 | $7.8 \times 10^{-8}$ |
| Comparison Y | 21 | 38 | 44 | $3.5 \times 10^{-7}$ |

[Comparison X]

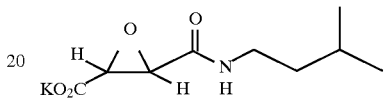

[Comparison Y]

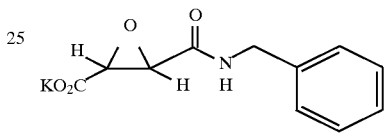

As is apparent from the above results, the epoxysuccinic acid derivative of the invention shows the bone resorption inhibitory action superior to the comparison compounds X and Y (which are described in Japanese Patent Publication No. 61-55509, page 14, Examples 61 and 62).

EXAMPLE 16

Cathepsin B Inhibitory Action

To 0.25 mL of a solution (pH: 6.0) containing 352 mM $KH_2PO_4$, 48 mM $Na_2HPO_4$, 5.32 mM EDTA.2 Na and 10 mM L-cysteine were added 0.1 mL of the lysosome fraction, 5 μL of the test compound solution, and 0.545 mL of distilled water. The mixture was preincubated at 30° C. for 15 minutes. Thereafter, the reaction was started by the addition of 0.1 mL of a solution of 50 μM carbobenzoxy-L-arginine-L-arginine-4-methylcoumaryl-7-amide (Z-Arg-Arg-MCA, substrate). The reaction was performed at 30° C. for 20 minutes, and then terminated by addition of 1 mL of an aqueous solution (pH: 4.3) containing 100 mM sodium monochloroacetate, 30 mM sodium acetate and 70 mM acetic acid. The finally obtained solution was subjected to measurement of fluorescence strength (excitation wavelength: 380 nm, emission wavelength: 460 nm). The results are set forth in the following Table 3.

TABLE 3

| Test Compound | Cathepsin B Inhibition ($IC_{50}$) |
|---|---|
| Example 3 | $2.3 \times 10^{-7}$ |
| Example 7 | $3.1 \times 10^{-7}$ |
| Example 13 | $2.0 \times 10^{-7}$ |

The above results indicate that the epoxysuccinic acid derivative of the invention has a cathepsin B inhibitory action in addition to the cathepsin L inhibitory action.

What is claimed is:

1. An epoxysuccinic acid derivative having the following formula and its salt:

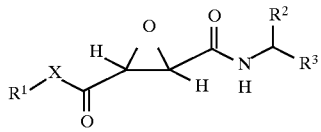

wherein $R^1$ represents a hydrogen atom, an alkyl group having 1 to 30 carbon atoms, an aryl group having 6 to 40 carbon atoms, or an aralkyl group having 7 to 40 carbon atoms; each of $R^2$ and $R^3$ independently represents an aryl group having 6 to 40 carbon atoms, an aralkyl group having 7 to 20 carbon atoms, or an alkyl group having 3 to 10 carbon atoms; X represents —O— or —NR$^4$—; and $R^4$ represents a hydrogen atom, an alkyl group having 1 to 10 carbon atoms, or an aralkyl group having 7 to 20 carbon atoms.

2. A pharmaceutical composition for inhibiting bone resorption, which comprises an epoxysuccinic acid derivative having the following formula and its salt;

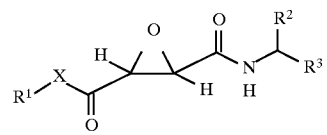

wherein $R^1$ represents a hydrogen atom, an alkyl group having 1 to 30 carbon atoms, and aryl group having 6 to 40 carbon atoms, or an aralkyl group having 7 to 40 carbon atoms; each of $R^2$ and $R^3$ independently represents an aryl group having 6 to 40 carbon atoms, an aralkyl group having 7 to 20 carbon atoms, or an alkyl group having 3 to 10 carbon atoms; X represents —O— or —NR$^4$—; and $R^4$ represents a hydrogen atom, an alkyl group having 1 to 10 carbon atoms, or an aralkyl group having 7 to 20 carbon atoms, and a pharmaceutically acceptable carrier.

3. A method for inhibiting bone resorption in a patient comprising administering to a patient a bone resorption inhibiting effective amount of the epoxysuccinic acid derivative of claim 1.

* * * * *